US 9,339,604 B1

(12) United States Patent
Moubayed

(10) Patent No.: US 9,339,604 B1
(45) Date of Patent: May 17, 2016

(54) INFUSION SYSTEMS WITH FAILURE AND ALARM TOLERANT OPERATING MODE

(71) Applicant: MAAS Technologies Holding, LLC, Laguna Hills, CA (US)

(72) Inventor: Ahmad-Maher Moubayed, Mission Viejo, CA (US)

( * ) Notice: Subject to any disclaimer, the term of this patent is extended or adjusted under 35 U.S.C. 154(b) by 141 days.

(21) Appl. No.: 14/185,573

(22) Filed: Feb. 20, 2014

Related U.S. Application Data

(60) Provisional application No. 61/766,998, filed on Feb. 20, 2013.

(51) Int. Cl.
*A61M 5/168* (2006.01)
*A61M 5/172* (2006.01)
*A61M 5/142* (2006.01)

(52) U.S. Cl.
CPC ........... *A61M 5/16827* (2013.01); *A61M 5/142* (2013.01); *A61M 5/16831* (2013.01); *A61M 5/16877* (2013.01); *A61M 5/1723* (2013.01); *A61M 2005/14208* (2013.01)

(58) Field of Classification Search
CPC ............ A61M 5/16827; A61M 5/142; A61M 5/16831; A61M 5/1723; A61M 5/168; A61M 5/16877; A61M 2005/14208
See application file for complete search history.

(56) References Cited

U.S. PATENT DOCUMENTS

| | | | | |
|---|---|---|---|---|
| 4,710,166 A | * | 12/1987 | Thompson | A61M 5/172 604/123 |
| 4,756,706 A | * | 7/1988 | Kerns | A61M 5/1413 128/DIG. 13 |
| 5,713,856 A | * | 2/1998 | Eggers | A61M 5/1413 604/65 |
| 2006/0064053 A1 | * | 3/2006 | Bollish | A61M 1/14 604/31 |
| 2010/0145303 A1 | * | 6/2010 | Yodfat | A61M 5/1408 604/506 |
| 2013/0177455 A1 | * | 7/2013 | Kamen | G06F 19/3418 417/313 |

* cited by examiner

*Primary Examiner* — Andrew Gilbert
(74) *Attorney, Agent, or Firm* — Robert D. Buyan; Stout, Uxa & Buyan, LLP

(57) ABSTRACT

Infusion systems and methods for infusing one or more drugs or other agents into the body of a human or animal subject. The system is programmed to take remedial action(s) upon sensing of a fault or error in connection with the infusion. In some embodiments, an agent may be infused through redundant flowpaths and, if a fault occurs in one flowpath, the system may respond by increasing flowrate through other non-faulting flowpath(s). In some embodiments, the fault may be a physiological reaction or symptom in the subject and the system may respond by adjusting or stopping flowrate(s) or one or more agents or changing the ratio of simultaneously infused agents.

8 Claims, 5 Drawing Sheets

INFUSION SYSTEMS WITH FAILURE AND ALARM TOLERANT OPERATING MODE

RELATED APPLICATION

This application claims priority to U.S. Provisional Patent Application No. 61/766,998 entitled Infusion Systems With Failure and Alarm Tolerant Operating Mode, filed Feb. 20, 2013, the entire disclosure of which is expressly incorporated herein by reference.

FIELD OF THE INVENTION

The present invention relates generally to medical devices and methods and more particularly to programmable infusion pump systems and their uses in the treatment of medical disorders.

BACKGROUND OF THE INVENTION

This invention relates in general to programmable infusion pumps that are used to deliver controlled infusions (e.g., intravenous infusions, epidural infusions, subcutaneous infusion, etc.) to patients in hospitals or out-of-hospital settings. Programmable infusion pumps are used to administer a wide range of drugs, analgesic medications, sedation drugs, biological therapies and other substances, including but not limited to cancer chemotherapy, Immune Globulin therapy, insulin, etc. Programmable infusion pumps typically include safety features that control or limit the rate of infusion and the amount of solution delivered to the patient, thereby preventing inadvertent overdosing, underdosing and/or infusion rate related side effects. Some programmable infusion pumps also include other safety features such as air-in-line detectors, occlusion detectors, etc.

The infusion systems of the prior art have included varying degrees of programmability and/or safety features. One particular use of programmable infusion pump technology is in administration of medications in a hospital setting. In a typical use case of programmable infusion pumps in hospital setting, the pump is programmed to deliver a medication to the patient at a specific rate of infusion. There are various safety features that are implemented in the design and operation of the infusion pump to mitigate against system fault that may result in overdosing, underdosing, air infusion and other faults including but limited to electronic memory fault, mechanical fault, etc.

Under normal operating conditions the programmable infusion pump will infuse the medication at the commanded rate of infusion, and the safety systems are engaged to detect various potential system faults. If a fault such as air-in-line, the infusion pump will stop and sound an alarm to notify the attending clinician such as the nurse about the fault. The nurse will respond to the pump to silence the alarm and correct the fault by manually removing the air from the infusion line following a standard procedure. In some cases the nurse response is delayed and the patient will experience a longer interruption of the infusion. In some other fault cases the infusion pump may have a fault that requires service, and the nurse will replace the infusion pump. Under these conditions, and with some medications such as antibiotics, the interruption of infusion may be tolerated by the patient. Fail safe mode of stopping an infusion and sounding an alarm when a fault is detected has been the general approach in programmable infusion pumps.

Generally, the infusion pump is not considered a life supporting device under the regulatory guidelines. However, in recent pharmaceutical developments new potent drugs have emerged that are considered in some cases as life supporting drugs.

There remains a need in the art for the development of new programmable infusion system that can reliably infuse life supporting drugs and can tolerate common faults detected of the prior art and will safely continue the delivery of medication to the patient without the interruption experienced in the prior art.

SUMMARY OF THE INVENTION

In accordance with the present invention there are provided infusion systems for infusing an infusate into the body of a human or animal subject, comprising: a) a first infusion flow path having a first pump apparatus for delivering infusate through the first infusion flow path and into the body of the subject; b) a second infusion flow path having a second pump apparatus for delivering infusate through the second infusion flow path and into the body of the subject; c) at least one sensor; and d) at least one controller in communication with said at least one sensor and said first and second pump apparatus. In such systems, the controller is programmed to i) initially cause infusate to be delivered through one or both of said first and second infusion flow paths such that the infusate is delivered into the subject's body at a desired total flow rate; ii) receive a fault signal from the sensor indicating the occurrence of a fault in one of the first and second infusion flow paths; and iii) in response to receipt of the fault signal, causing delivery of infusate through the faulting flow path to cease and adjusting the flow rate of infusate through the other flow path such that infusate continues to be delivered into the subject's body at the desired total flow rate. As used in this patent application, the term "fault" is used to refer to various types of actual or impending faults, errors, undesirable occurrences, problems, etc. associated with either the infusion system or the subject. In some embodiments, the fault may be sensed by a sensor located on the infusion system (e.g., a device that monitors for air bubbles or tubing disruptions). In other embodiments, the fault may be sensed by a sensor that monitors the subject for physiological changes indicative of an overdose, iteration, reaction, etc. (e.g., a vital signs monitor). In this embodiment, the "fault" is sensed in one of the first or second flowpaths, so the sensor would be some type of sensor (e.g., an air bubble detector, flowmeter, etc.) that senses a fault, error, undesirable occurrence, problem, etc. associated with either the first flowpath or the second flowpath.

Further in accordance with the present invention, there are provided systems for alternate infusion of a first infusate or a second infusate into the body of a human or animal subject, comprising: a) a first infusion flow path connected to a source of the first infusate and having a first pump apparatus for delivering the first infusate through the first infusion flow path and into the body of the subject; b) a second infusion flow path connected to a source of the second infusate and having a second pump apparatus for delivering the second infusate through the second infusion flow path and into the body of the subject; c) at least one sensor; and d) at least one controller in communication with said at least one sensor and said first and second pump apparatus. In such systems, the controller is programmed to i) initially cause the first infusate to be delivered through the first flow path while none of the second infusate is being delivered through the second flowpath; ii) receive a fault signal from the sensor indicating the occurrence of a fault; and iii) in response to receipt of the fault signal, cease delivery of the first infusate through the first infusate flow path and commence delivery of the second infusate through the second flow path to occur. As noted above, the term "fault" is used herein to refer to various types of actual or impending faults, errors, undesirable occurrences, problems, etc. associated with either the infusion system or the subject. In some embodiments, the fault may be sensed by a sensor located on the infusion system (e.g., a device that monitors for air bubbles or tubing disruptions). In other embodiments, the fault may be sensed by a sensor that monitors the subject for physiological changes indicative of an overdose, iteration, reaction, etc. (e.g., a vital signs monitor). In this particular embodiment, the "fault" is some occurrence or impending occurrence that makes it desirable to stop infusing the first infusate and begin infusing the second infusate. For example, in this embodiment, the "fault" may be an indication from a vital signs monitor or other physiological sensor that the subject is exhibiting signs of an overdose or adverse effect of the first infusate and the subsequent infusion of the second infusate may reverse or treat the overdose or adverse effect of the first infusate.

Still further in accordance with the present invention, there are provided systems for ratiometric co-infusion of a first infusate and a second infusate into the body of a human or animal subject, comprising: a) a first infusion flow path connected to a source of the first infusate and having a first pump apparatus for delivering the first infusate through the first infusion flow path and into the body of the subject; b) a second infusion flow path connected to a source of the second infusate and having a second pump apparatus for delivering the second infusate through the second infusion flow path and into the body of the subject; c) at least one sensor; and d) at least one controller in communication with said at least one sensor and said first and second pump apparatus. In such systems, the controller is programmed to i) initially cause the first infusate to be delivered through the first flow path at a first infusate flow rate and the second infusate to be delivered through the second flow path at a second infusate flow rate; ii) receive a fault signal from the sensor indicating the occurrence of a fault; and iii) in response to receipt of the fault signal, modifying the first infusate flow rate and/or the second infusate flow rate to thereby change the ratio of the first infusate flow rate to the second infusate flow rate. Again, as noted above, the term "fault" is used herein to refer to various types of actual or impending faults, errors, undesirable occurrences, problems, etc. associated with either the infusion system or the subject. In some embodiments, the fault may be sensed by a sensor located on the infusion system (e.g., a device that monitors for air bubbles or tubing disruptions). In other embodiments, the fault may be sensed by a sensor that monitors the subject for physiological changes indicative of an overdose, iteration, reaction, etc. (e.g., a vital signs monitor). In this particular embodiment, the "fault" is some occurrence or impending occurrence indicating that some adjustment of the ratio of the first infusate flow rate to the second infusate flow rate is desirable. For example, in this embodiment, the "fault" may be sensed by a sensor (such as a vital signs monitor or other physiological or chemical monitor) indication that the relative doses of the first and second infusates are less than optimal or that too much of one drug or the other is being administered. For example, the effects of certain drugs may be additive or supra-additive when the drugs are co-administered and the detected "fault" may be an indication that the combined effects of the co-administered drugs is sub-optimal or that too much of one drug or the other is being administered thereby resulting in some adverse effect that may be improved or remedied by adjusting the ratio of the first infusate flow rate to the second infusate flow rate.

Still further in accordance with the present invention, there are provided methods for using the above-summarized systems.

Further examples, aspects and details of the present invention will be apparent to those of skill in the art upon reading of the detailed description, examples and claim statements set forth below.

DETAILED DESCRIPTION

The following detailed description and the accompanying drawings are intended to describe some, but not necessarily all, examples or embodiments of the invention. The contents of this detailed description and the accompanying drawings are not necessarily all-inclusive and do not limit the scope of the invention in any way.

Figure 1:
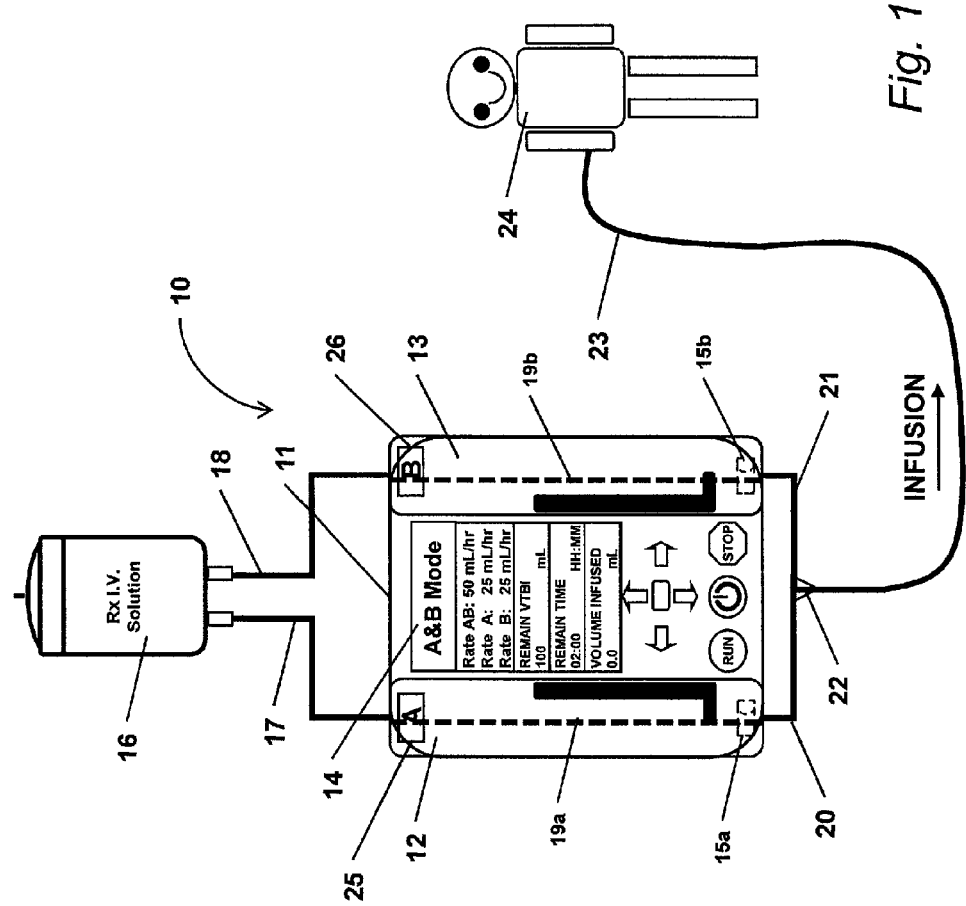
FIG. 1 is a diagram showing the manner in which an infusion system of the present invention may be operated in a Failure/Alarm Tolerant Mode—Normal Operating State.
Figure 2:
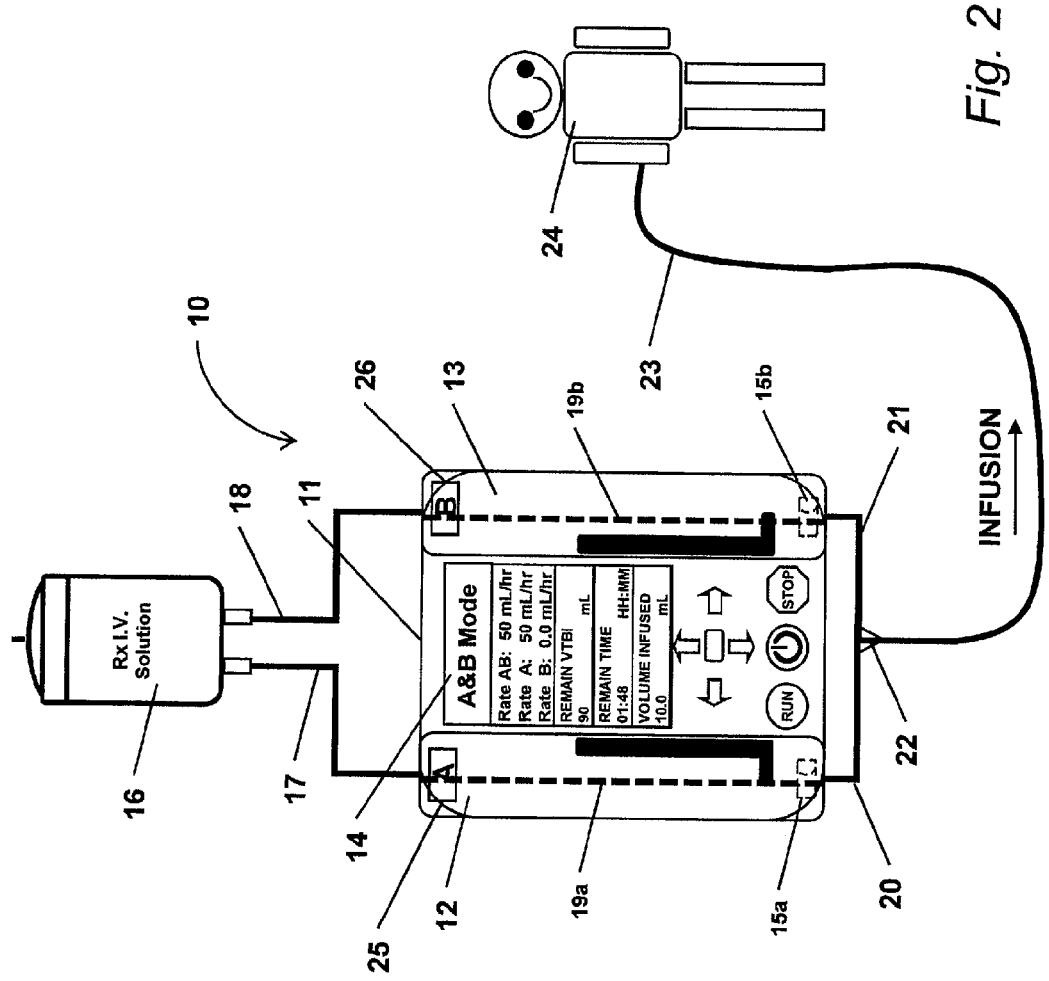
FIGS. 2 and 2A are diagrams showing the manner in which an infusion system of the present invention may be operated in Failure/Alarm Tolerant Mode—Alarm/Failure Operating State for delivery of a single agent.

FIG. 1 and FIG. 2 shows a programmable infusion system 10 of the present invention which comprises the following components:
- 10 Programmable Infusion System
- 11 Infusion pump—dual channel
- 12 Channel A pump head
- 13 Channel B pump head
- 14 LCD display
- 15 Air detection sensor—one sensor for each channel
- 16 Prescription drug I.V. solution bag
- 17 Tubing from I.V. bag to channel A for medication delivery to the patient.
- 18 Tubing from I.V. bag to channel B for medication delivery to the patient.
- 19 Tubing placed into the pump head to be operated on by the pumping mechanism—channel A and Channel B
- 20 Tubing Exiting Channel A
- 21 Tubing Exiting Channel B
- 22 Tubing fitting connecting tubing sections from Channel A and Channel B into a single tubing for medication delivery to the patient
- 23 Tubing section delivering medication through Channel A& B to the patient.
- 24 Patient
- 25 Indicator for Channel A operating state (Green is Normal & Red is Alarm)
- 26 Indicator for Channel B operating state (Green is Normal & Red is Alarm)

In the example of FIG. 1, the programmable infusion system 10 generally comprises a dual channel programmable infusion pump 11 with its controller, having channel A pump head 12 with its own controller, and channel B pump head 13 with its own controller, an infusate-containing vessel 16, an input tubing component 17 for channel A, an input tubing component 18 for channel B, an output tubing component 20 for channel A, an output tubing component 21 for channel B, a connecting fitting 22, a tubing component 23 to the patient site, an air-in-line detector 15a for channel A, an air-in-line detector 15b for channel B, a tubing pumping segment 19a for channel A, a tubing pumping segment 19b for channel B, a user interface such as touch screen and keypad 14, a status display 25 for channel A, and status display 26 for channel B. It will be appreciated that the pump head of channel A and channel B may be any suitable type of pump such as traditional peristaltic pumps.

FIG. 1 shows the infusion system 10 operating two channels A and B to infuse a single drug in a fault tolerant mode under normal operating state. As an example of a use case scenario, the infusion system is programmed to infuse, the infusate (e.g. a life supporting medication) at a rate of 50 mL/hr. Each of the pump head channels A and B will run independently and concurrently at a rate of 25 mL/hr to deliver a combined flow rate of 50 mL/hr through tubing segment 23 to the patient 24. This will be a normal operating state with no faults and/or alarms.

FIG. 2 shows the infusion system 10 described in FIG. 1 with the event of fault detection on channel B. In FIG. 2, when the fault is detected, the pump head controller of channel B, running at the rate of 25 mL/hr, will stop the infusion and issue an alarm status. Then the pump head controller of channel A will be commanded to increase the rate of infusion on channel A from 25 mL/hr to 50 mL/hr while the channel B pump head is stopped. This will ensure an accurate and uninterrupted delivery of medication to the patient as prescribed. This fault tolerant mode of delivery of 50 mL/hr on channel A will continue until the fault condition is cleared on channel A by the attending nurse or clinician. When the fault and alarm are cleared, the programmable infusion pump will revert back to normal operation, and continuing medication delivery on channel A and channel B concurrently at the rate of 25 mL/hr on each channel for a combined rate of 50 mL/hr through tubing segment 23 to the patient 24.

Figure 2A:
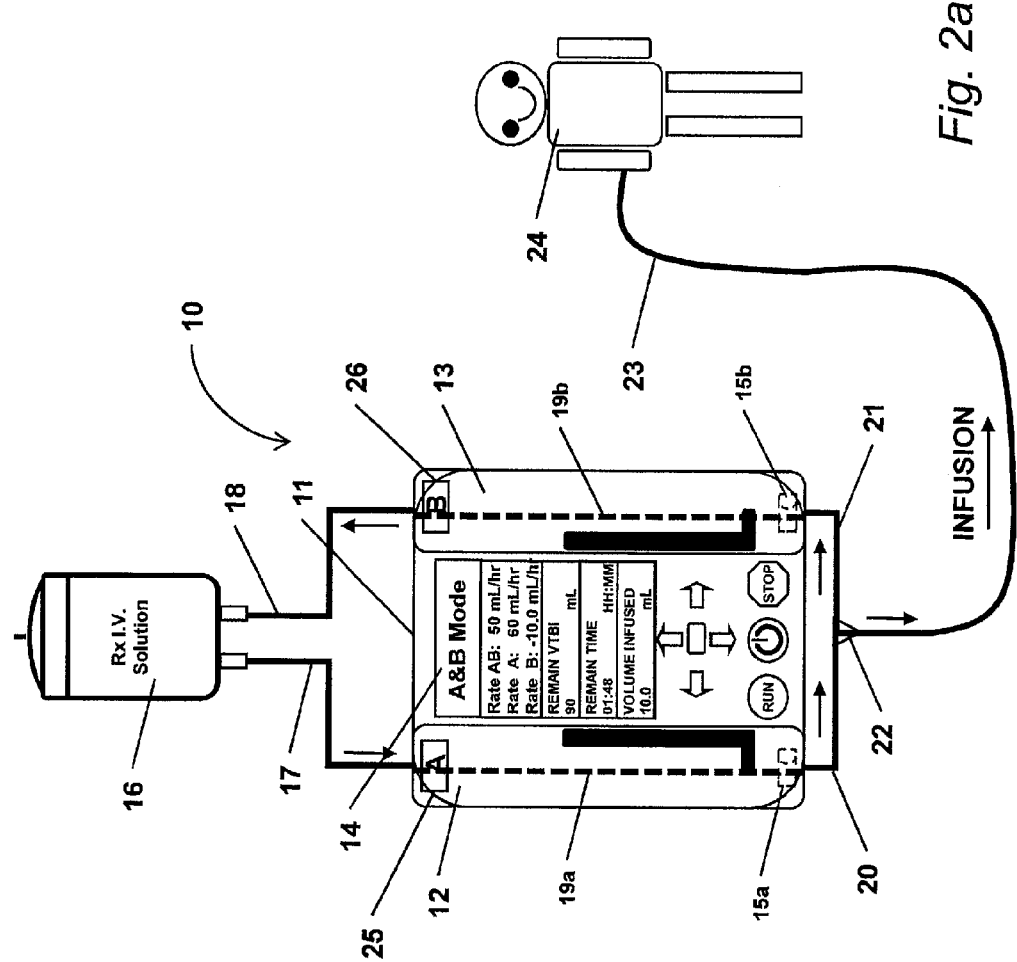

In another example illustrated in FIG. 2a, the fault detected in channel B is due to an air-in-line detection, where an air bolus may have formed and accumulated due to outgassing of the infusate in the pumping segment 19b. In this event, where the infusion rate of channel A is 25 mL/hr and channel B is 25 mL/hr for a combined infusion rate of 50 mL/hr to the patient, the infusion on channel B will stop and reverse the flow at 10 mL/hr, while the rate on channel A will increase from 25 mL/hr to 60 mL/hr. This will allow the net infusion rate to the patient to continue at the prescribed rate of 50 mL/hr and allows the air bolus in the pumping segment 19b of channel B to gravitate towards the vessel 16. This mode of operation will continue for a short period of time sufficient to allow for the flow of the air bolus through the input segment 18 to the vessel 16. After this fault correction, the system can revert back to the normal operation.

Figure 3:
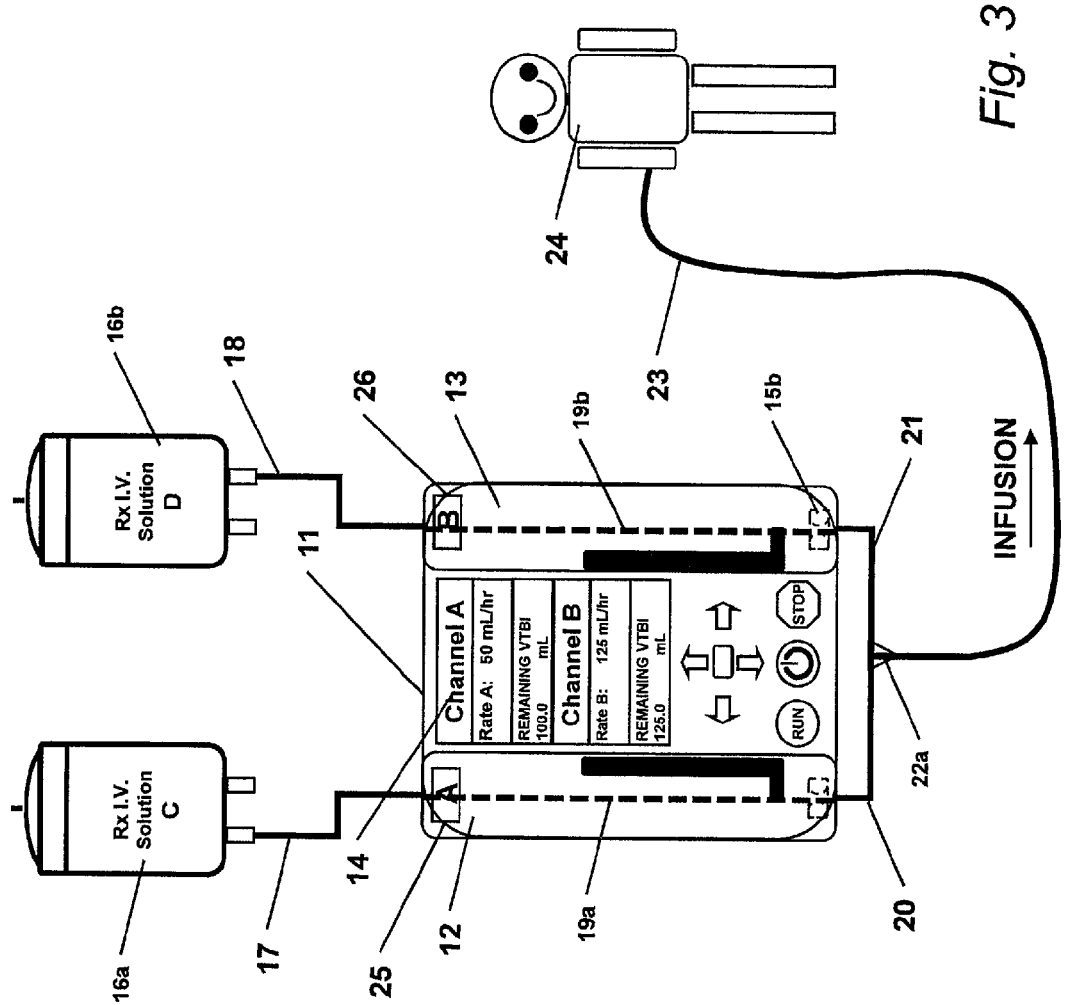
FIG. 3 is a diagram showing the manner in which an infusion system of the present invention may be operated in an Independent Dual Channel Delivery Mode for delivery of two separate agents.

FIG. 3 illustrates the infusion system 10 operating in an independent dual channel mode. In this example, the system includes the same components as the system shown in FIG. 1 with independent dual channel drug delivery mode. Channel A and channel B are programmed to operate independent of one another, where channel A is programmed to infuse, infusate C in vessel 16a at a rate of 50 mL/hr, and channel B is programmed to infuse, infusate D in vessel 16b at a rate of 125 mL/hr. Illustrated is tubing segment 20 connecting the output of pump head 12 to fitting 22a, and the tubing segment 21 connecting the output of pump head 13 to fitting 22a. The fitting 22a connecting each of tubing segments 20 and 21 to a dual lumen tubing segment 23 to transfer the infusates C and D separately to patient 24.

Figure 4:
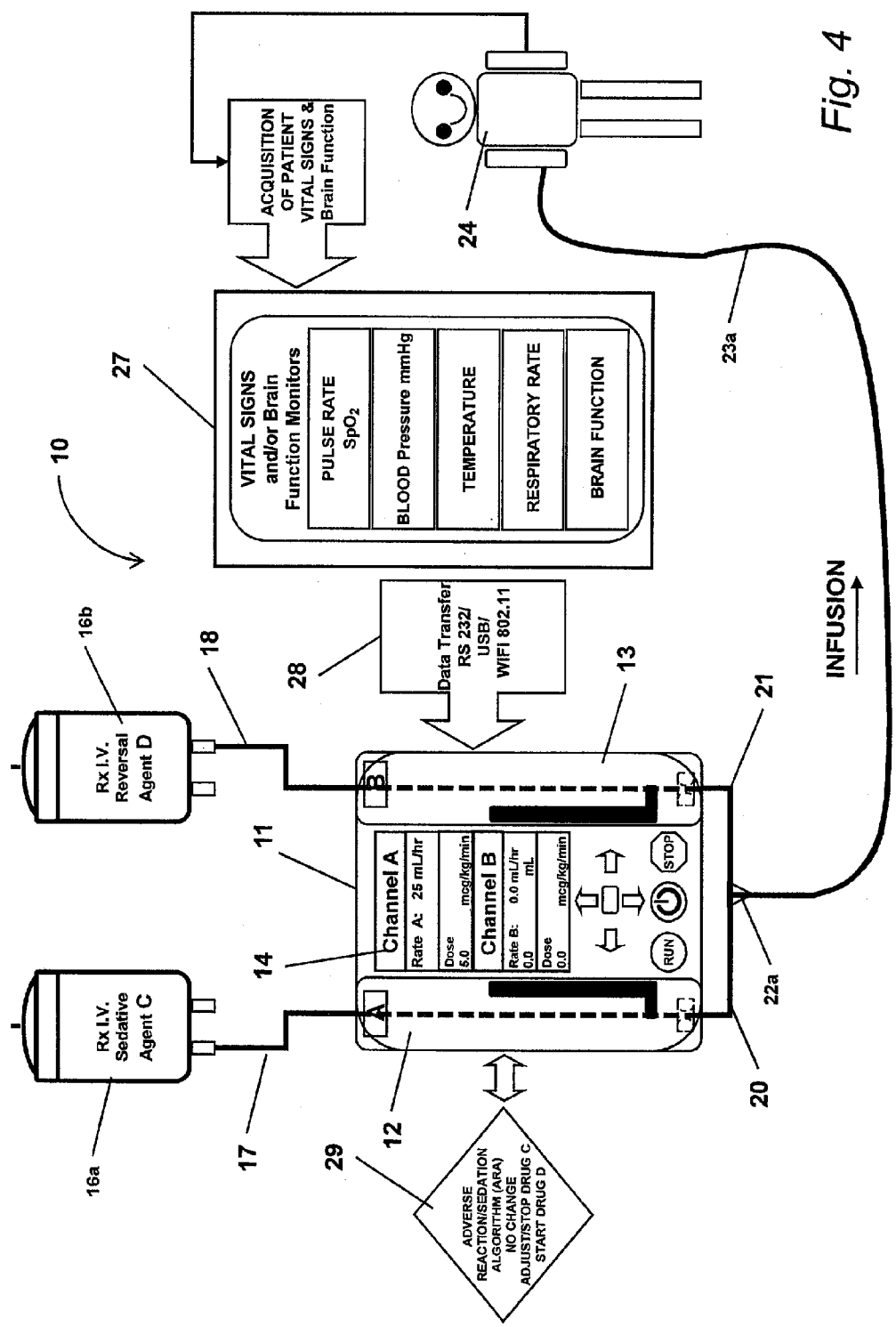
FIG. 4 is a diagram showing the manner in which an infusion system of the present invention may be operated in an Interdependent Dual Channel Drug Delivery Mode with a Feedback Loop.

In yet another embodiment of this invention illustrated in FIG. 4, the programmable infusion system 10 operates in an interdependent dual channel drug delivery mode with feedback loop. In the example of FIG. 4, the system includes the same components as the system 10 shown in FIG. 1 and, in addition, includes the following:
- 27 Vital Signs monitoring equipment acquiring patient vital signs data
- 28 Communication link for data transfer from vital signs monitoring equipment to the infusion pump.
- 29 Algorithm built into the infusion system the will analyze the data from the vital signs monitors and command the infusion rate for the two channels A and B.

This interdependent dual channel drug delivery mode with feedback loop is suitable for the infusion of sedative and analgesic drugs that may cause complications including cardiorespiratory compromise. Some of the commonly used sedative drugs (e.g. Fentanyl), which may cause cardiorespiratory complications, have reversal agents (e.g. Naloxone is a reversal agent for Fentanyl). These reversal agents are administered to reverse the over sedation of the sedative drug in the event the patient receiving the sedation experiences cardiorespiratory complications such as respiratory depression. In this invention illustrated in FIG. 4, the programmable infusion system 10 generally comprises a dual channel programmable infusion pump 11 with its controller, having channel A pump head 12 with its own controller, channel B pump head 13 with its own controller, and user interface such as a touch screen and keypad 14, an infusate vessel 16a containing a sedative drug agent C, an infusate vessel 16b containing a reversal drug agent D, a tubing segment 17 connecting vessel 16a to the input of pump head 12, a tubing segment 18 connecting vessel 16b to the input of pump head 13, a tubing segment 20 connecting the output of pump head 12 to a fitting 22a, a tubing segment 21 connecting the output of pump head 13 to a fitting 22a, a fitting 22a connecting each of tubing segments 20 and 21 to a dual lumen tubing segment 23a, a dual lumen tubing segment 23a to transfer sedative agent C and reversal agent D separately to patient 24, a set of vital signs monitors 27 including but not limited to pulse oximeter, blood pressure monitor, respiratory rate monitor, etc. acquiring vital signs data from patient 24, a data transfer means 28 including but not limited to wired transfer e.g. RS 232 serial port and/or wireless transfer e.g. WiFi 802.11 and Bluetooth to establish communication between the vital signs monitors 27 and the infusion pump 11, a controller of the infusion pump having an algorithm 29 to decide on the infusion rates, within a pre-set parameters, of sedative agent C in vessel 16a and reversal agent D in vessel 16b.

In this embodiment of the invention illustrated in FIG. 4 the programmable infusion pump 11 is programmed to infuse sedative agent C from vessel 16a utilizing pump head 12 (channel A) at a pre-set infusion rate or range of rates, and to infuse reversal agent D from vessel 16b utilizing pump head 13 at a pre-set infusion rate or range of rates. The output tubing segment 23a is connected to the patient 24 usually intravenously or epidural for drug delivery. The patient 24 is also connected to various sensors to detect and monitor vital signs through a set of vital signs monitors 27. When the procedural sedation in the acute care setting in the hospital starts, the programmable pump 11 will start infusing sedative agent C from vessel 16a to the patient 24 utilizing pump head 12 (channel A) at a set ramp-up rate, while pump head 13 (channel B) is on standby zero infusion rate. The patient 24 is monitored for sedation via various vital signs monitors 27. When optimal sedation levels are achieved as indicated by the vital signs monitors 27, the data received by the programmable infusion pump 11 via data transfer means 28 is analyzed by the controller algorithm 29, and the infusion rate on pump head 12 (channel C) will be maintained at a steady rate. In the event of an adverse reaction of over-sedation, the vital signs monitors will issue an alarm and continuous stream of data received by the programmable pump 11 via data transfer means 28 is analyzed by the controller algorithm 29 and the pump head 12 (channel A) will be commanded to stop the infusion of sedative agent C in vessel 16a and the pump head 13 (channel B) will be commanded to initiate and start the infusion of reversal agent D in vessel 16b while the patient 24 continues to be monitored to reverse the over-sedation adverse reaction and stabilize the patient.

It will be appreciated that the pump head of channel A and channel B of the invention illustrated in FIG. 4 may be of a syringe drive type, and the vessel for the infusate is a syringe.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. An infusion system for infusing an infusate into the body of a human or animal subject, said system comprising:
    a first infusion flow path having a first pump apparatus for delivering infusate through the first infusion flow path and into the body of the subject;
    a second infusion flow path having a second pump apparatus for delivering infusate through the second infusion flow path and into the body of the subject;
    at least one sensor; and
    at least one controller in communication with said at least one sensor and said first and second pump apparatus;
    wherein said at least one controller is programmed to:
    i) initially cause infusate to be delivered through one or both of said first and second infusion flow paths such that the infusate is delivered into the subject's body at a desired total flow rate;
    ii) receive a fault signal from the at least one sensor indicating the occurrence of a fault in one of the first or second infusion flow paths; and
    iii) in response to receipt of the fault signal, causing delivery of infusate through the faulting flow path to cease and adjusting the flow rate of infusate through the other flow path such that infusate continues to be delivered into the subject's body at the desired total flow rate.

2. A system according to claim 1 wherein said at least one controller initially causes concurrent delivery of a first portion of the desired total flow rate through the first infusion flow path and a second portion of the desired total flow rate through the second infusion flow path and, in response to receipt of a fault signal, causes flow of infusate through the faulting flow path to cease and flow of infusate through the other flow path to increase by the amount that was originally being delivered through the faulting flow path, thereby continuing to deliver infusate to the subject's body at the desired total flow rate.

3. A system according to claim 1 wherein said at least one controller is further programmed to:
    cause remedial action to be undertaken to remedy the fault in the faulting flow path.

4. A system according to claim 3 wherein the fault comprises detected unwanted air in the faulting flow path and said at least one controller is programmed to reverse the pumping apparatus on the faulting flow path for a period of time in an attempt to clear the detected unwanted air from the faulting flow path.

5. A system according to claim 4 wherein said at least one controller is further programmed to cause the non-faulting pump to concurrently increase the flow rate through the non-faulting flow path to compensate for the negative flow through the faulting flow path while attempting to clear unwanted air.

6. A system according to claim 3 wherein:
    said at least one sensor is operative to send a fault remedied signal to the controller is the remedial action successfully remedies the fault; and
    the controller is further programmed such that, in response to receipt of a fault remedied signal, the controller will re-adjust flow of infusate through the first and second flowpaths to again cause a first portion of the desired total flow rate to be delivered through the first flow path and a second portion of the desired total flow rate to be delivered through the second flow path.

7. A method for infusion of an infusate, comprising the steps of:
    obtaining or providing an infusion system according to claim 1;
    connecting the first and second flow paths to a source of infusate;
    connecting the first and second flow paths to the body of a human or animal subject; and,
    operating the system.

8. A method according to claim 5 wherein both the first and second flow paths are connected to a common vessel containing the infusate.

* * * * *